(12) United States Patent
Kim et al.

(10) Patent No.: US 11,635,421 B2
(45) Date of Patent: Apr. 25, 2023

(54) SAP EVALUATION APPARATUS

(71) Applicant: LG Chem, Ltd., Seoul (KR)

(72) Inventors: Yeon Soo Kim, Daejeon (KR); Hye Mi Nam, Daejeon (KR); Hyunsup Lee, Daejeon (KR); Sang Gi Lee, Daejeon (KR); Chang Hun Han, Daejeon (KR); Myung Han Lee, Daejeon (KR); Hyejin Han, Daejeon (KR)

(73) Assignee: LG Chem, Ltd.

( * ) Notice: Subject to any disclaimer, the term of this patent is extended or adjusted under 35 U.S.C. 154(b) by 994 days.

(21) Appl. No.: 16/466,890

(22) PCT Filed: Aug. 24, 2018

(86) PCT No.: PCT/KR2018/009823
§ 371 (c)(1),
(2) Date: Jun. 5, 2019

(87) PCT Pub. No.: WO2019/039916
PCT Pub. Date: Feb. 28, 2019

(65) Prior Publication Data
US 2020/0088710 A1     Mar. 19, 2020

(30) Foreign Application Priority Data

Aug. 25, 2017 (KR) .......................... 10-2017-0108178
Sep. 21, 2017 (KR) .......................... 10-2017-0121928

(51) Int. Cl.
*G01N 33/32* (2006.01)
*A61F 13/53* (2006.01)
(Continued)

(52) U.S. Cl.
CPC ............. *G01N 33/32* (2013.01); *A61F 13/53* (2013.01); *G01N 15/088* (2013.01); *A61F 2013/530481* (2013.01); *G01N 2015/0034* (2013.01)

(58) Field of Classification Search
CPC ............ G01N 2015/0034; A61F 2013/530744
See application file for complete search history.

(56) References Cited

U.S. PATENT DOCUMENTS

| 5,797,893 A | 8/1998 | Wada et al. |
| 5,803,920 A | 9/1998 | Gilman |

(Continued)

FOREIGN PATENT DOCUMENTS

| CA | 2315748 A1 | 7/1999 |
| CN | 103339152 A | 10/2013 |

(Continued)

OTHER PUBLICATIONS

Chinese Search Report for Application No. 201880004741.3 dated Sep. 22, 2020, 2 pages.

(Continued)

*Primary Examiner* — Daniel S Larkin
(74) *Attorney, Agent, or Firm* — Lerner David LLP

(57) ABSTRACT

A SAP evaluation apparatus includes: a main body installed with a lifting bar that is raised or lowered; a container portion installed under the lifting bar in the main body and having an internal containing space for containing an absorber; an operating portion connected to the lifting bar and having a lifting plate that is raised or lowered within the containing space and applies pressure to the absorber and an injection portion for injecting an ink in the direction of the absorber; a dispersion measurement portion for measuring the dispersion of the ink through the absorber; and a controller installed at the main body to measure absorption of (Continued)

the ink into the absorber and measure swelling capacity of the absorber while the ink is injected into the absorber.

12 Claims, 9 Drawing Sheets

(51) Int. Cl.
*G01N 15/08* (2006.01)
*G01N 15/00* (2006.01)

(56) References Cited

U.S. PATENT DOCUMENTS

| | | | |
|---|---|---|---|
| 2004/0014226 | A1 | 1/2004 | Schrof et al. |
| 2004/0024375 | A1 | 2/2004 | Litvay |
| 2004/0215160 | A1* | 10/2004 | Chmielewski .... A61F 13/15658 604/367 |
| 2007/0106013 | A1* | 5/2007 | Adachi ............... A61L 15/60 524/556 |
| 2007/0207924 | A1 | 9/2007 | Ikeuchi et al. |
| 2007/0264489 | A1 | 11/2007 | Sasabe et al. |
| 2008/0119586 | A1* | 5/2008 | Byerly ............... A61L 15/60 523/111 |
| 2012/0318046 | A1* | 12/2012 | Ehrnsperger ....... G01N 15/0826 73/38 |
| 2013/0274088 | A1 | 10/2013 | Handa et al. |
| 2014/0141970 | A1 | 5/2014 | Konishi et al. |
| 2015/0218341 | A1 | 8/2015 | Nakashima et al. |
| 2016/0220724 | A1 | 8/2016 | Ka et al. |
| 2016/0327496 | A1 | 11/2016 | Nakayama et al. |
| 2017/0216817 | A1 | 8/2017 | Torii et al. |
| 2017/0326528 | A1* | 11/2017 | Park .................. B01J 20/3021 |
| 2018/0001300 | A1* | 1/2018 | Nakatsuru ........... B01J 20/3085 |

FOREIGN PATENT DOCUMENTS

| | | |
|---|---|---|
| CN | 104582832 A | 4/2015 |
| CN | 105849538 A | 8/2016 |
| CN | 105973760 A | 9/2016 |
| CN | 106715543 A | 5/2017 |
| CN | 106872315 A | 6/2017 |
| EP | 2674441 A1 | 12/2013 |
| JP | H02208543 A | 8/1990 |
| JP | H0847685 A | 2/1996 |
| JP | H09157534 A | 6/1997 |
| JP | 2003088551 A | 3/2003 |
| JP | 2015188709 A | 11/2015 |
| JP | 2016120083 A | 7/2016 |
| JP | 2016214804 A | 12/2016 |
| KR | 20010033707 A | 4/2001 |
| KR | 100462735 B1 | 12/2004 |
| KR | 20060027360 A | 3/2006 |
| KR | 100944467 B1 | 3/2010 |
| KR | 20150062959 A | 6/2015 |
| KR | 101559755 B1 | 10/2015 |
| KR | 101596624 B1 | 2/2016 |
| KR | 20160094535 A | 8/2016 |
| KR | 101670403 B1 | 10/2016 |
| KR | 20170103849 A | 9/2017 |
| WO | 01030290 A1 | 5/2001 |
| WO | 02039093 A1 | 5/2002 |
| WO | 2016111223 A1 | 7/2016 |

OTHER PUBLICATIONS

International Search Report including the Written Opinion for Application No. PCT/KR2018/009823 dated Nov. 29, 2018.
Chatterjee et al., Chapter VIII—Synthetic Superabsorbents, Absorbent Technology, Mar. 2002, pp. 283-322, Elsevier Science B.V., XP055645971, Retrieved from the Internet <https://www.elsevier.com/books/absorbent-technology/chatterjee/978-0-444-50000-7>.
Extended European Search Report including Written Opinion for Application No. EP18847726.9, dated Dec. 3, 2019, pp. 1-14.

* cited by examiner

【Figure 1】
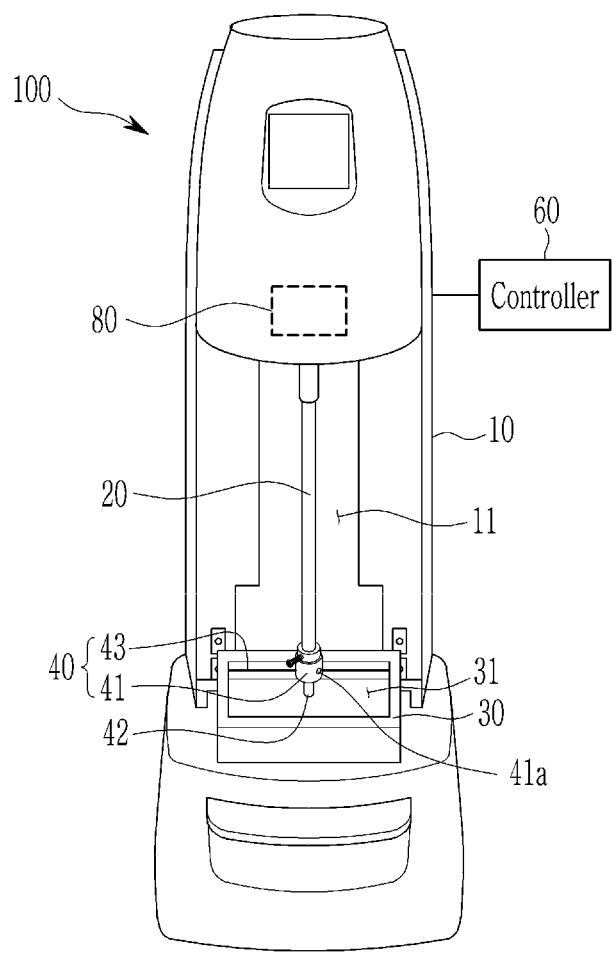

[Figure 2]
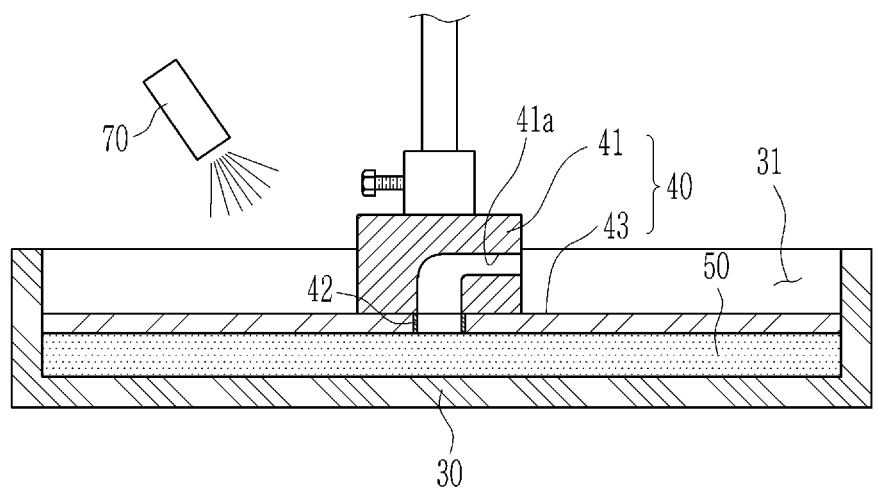
[Figure 3]
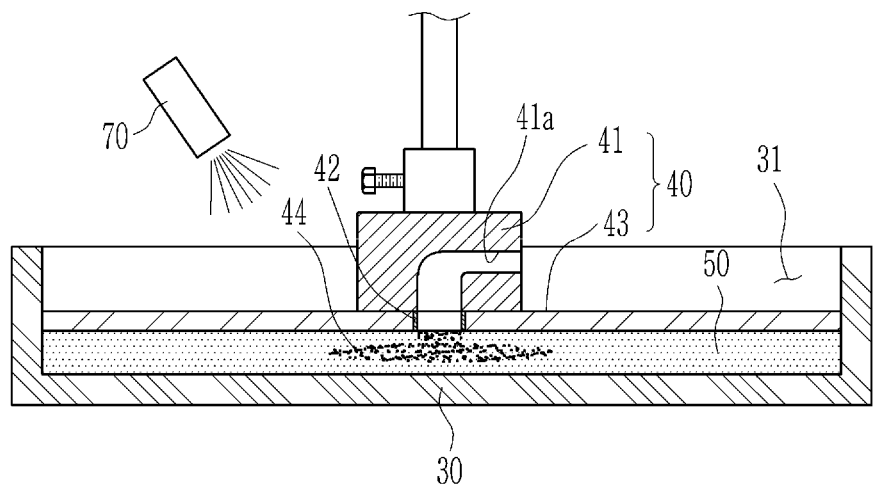

[Figure 4]
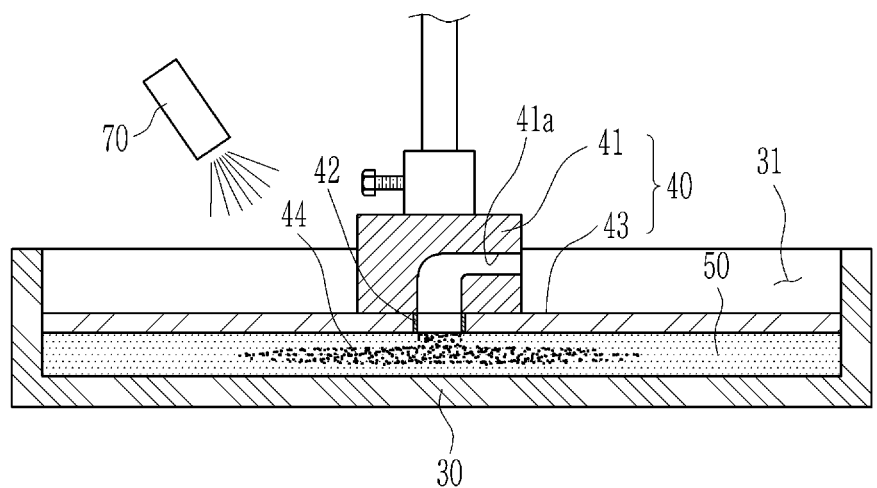
[Figure 5]
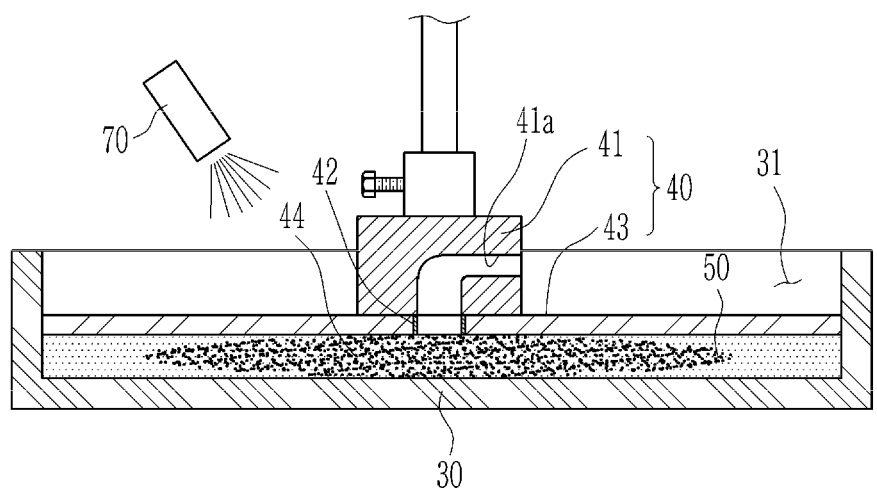

[Figure 6]
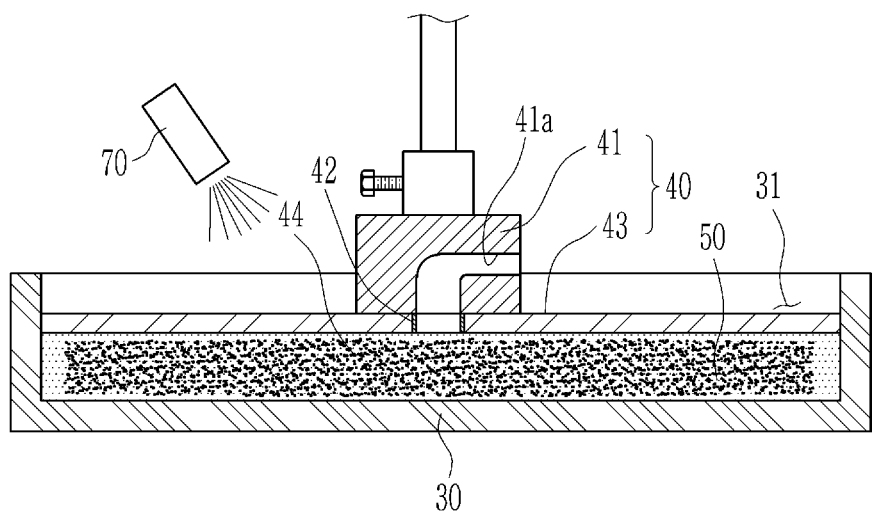
[Figure 7]
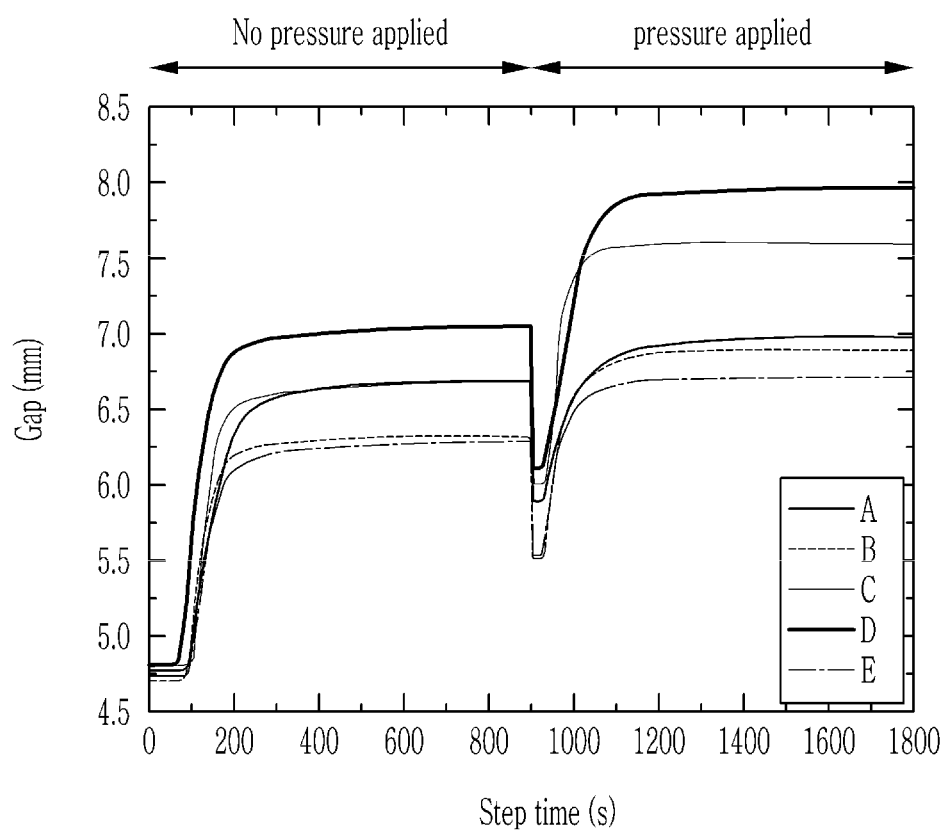

[Figure 8]
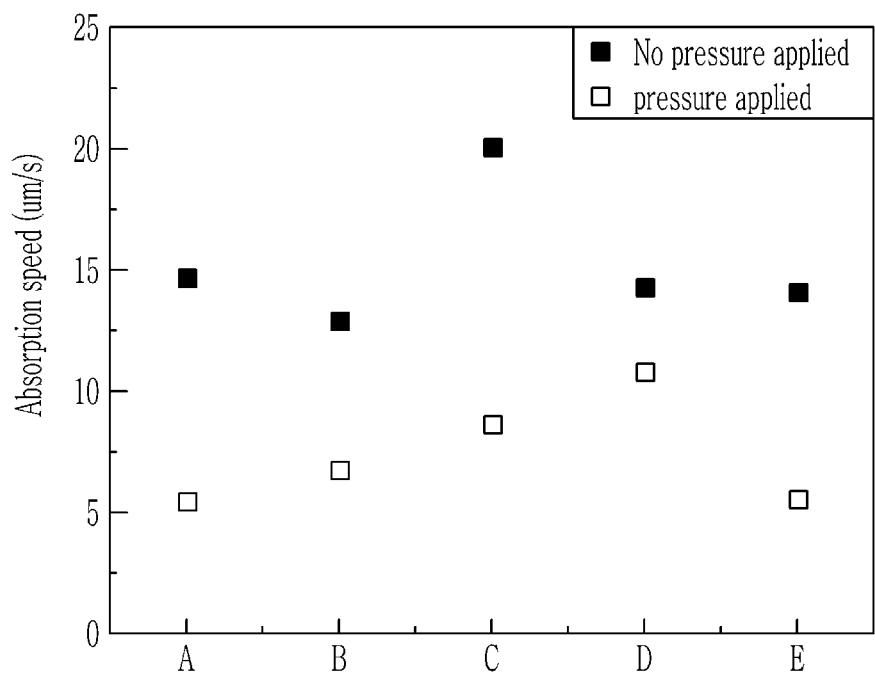
[Figure 9]
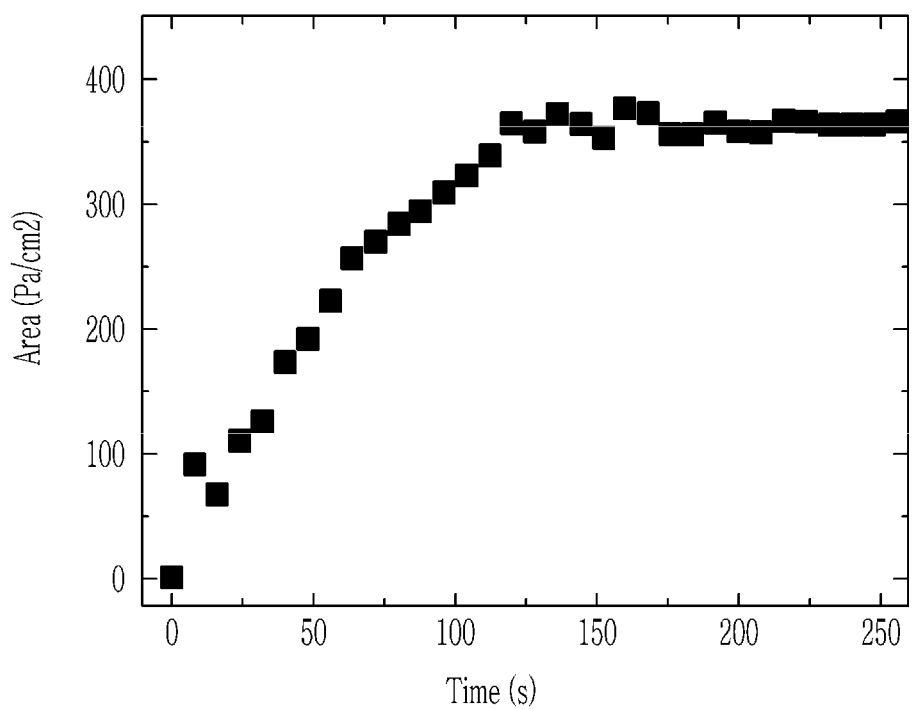

[Figure 10]
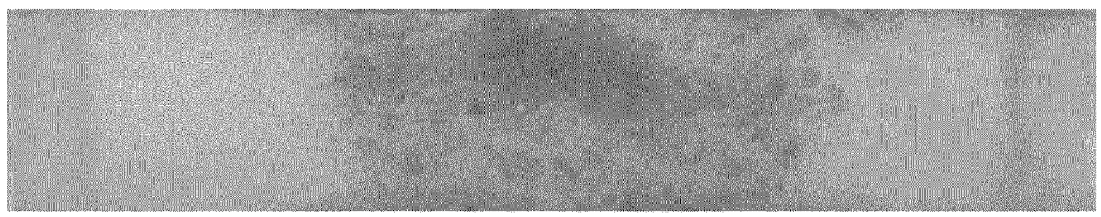
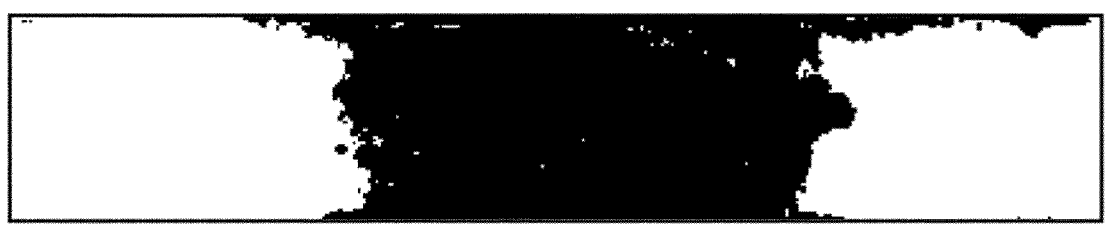
[Figure 11]
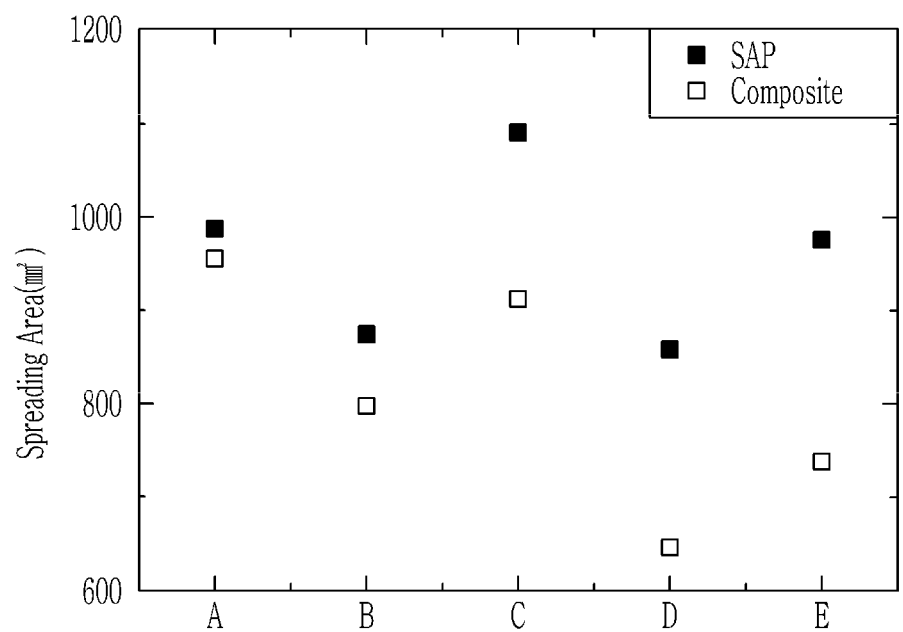

【Figure 12】
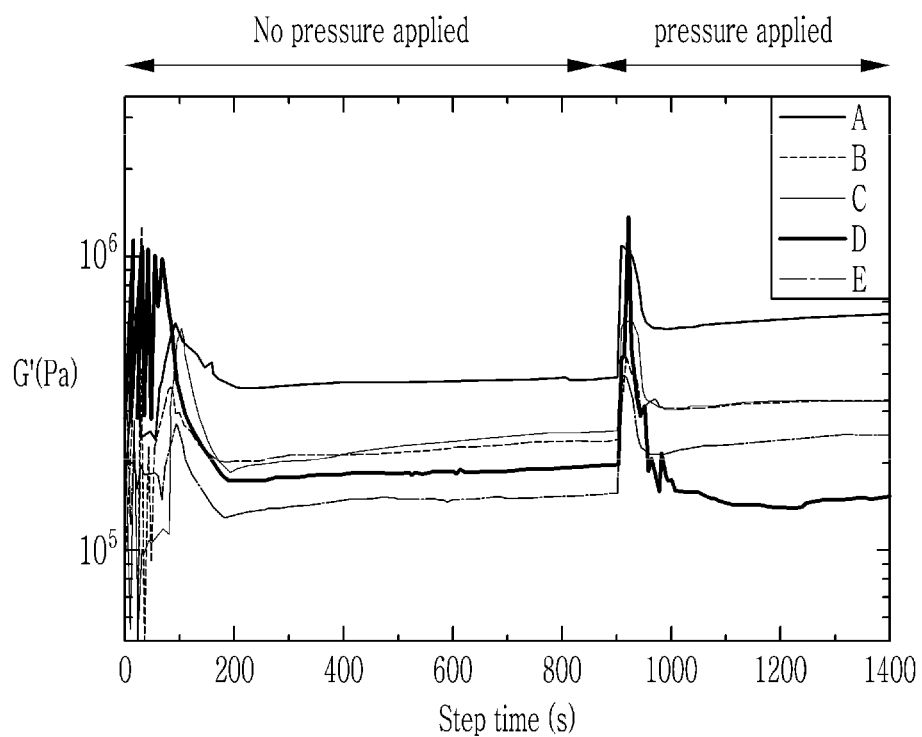
【Figure 13】
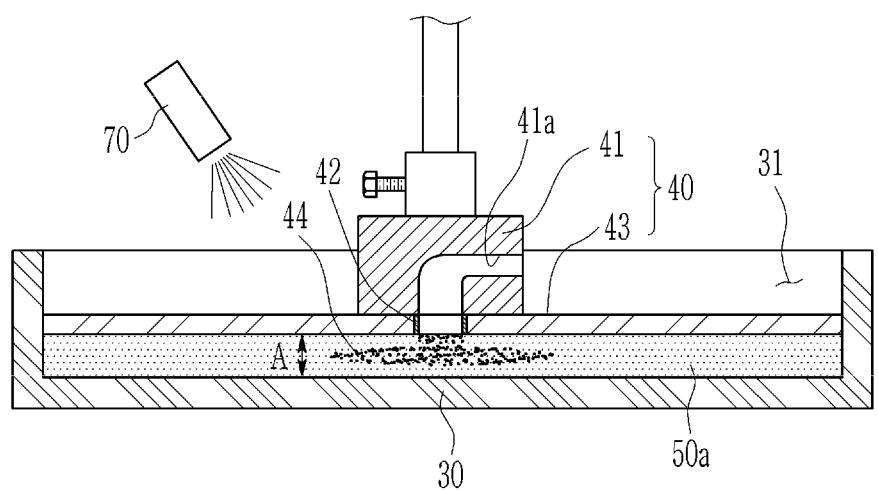

【Figure 14】
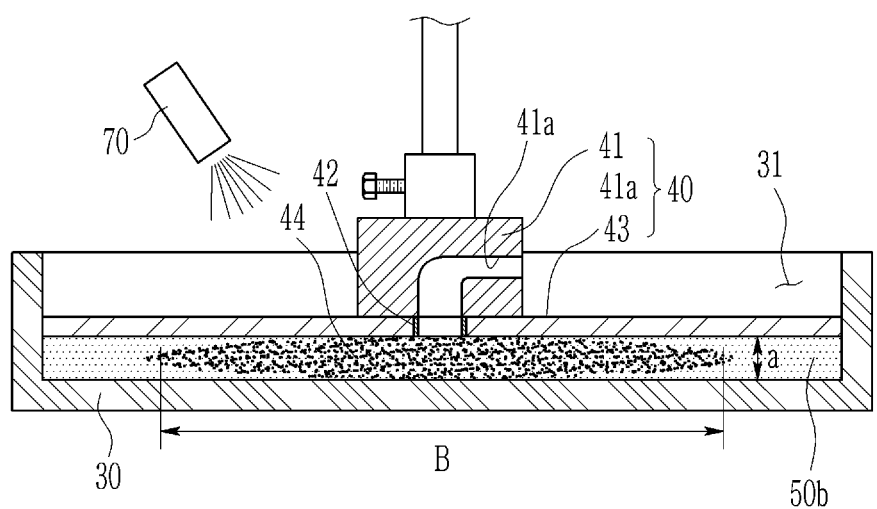

[Figure 15]
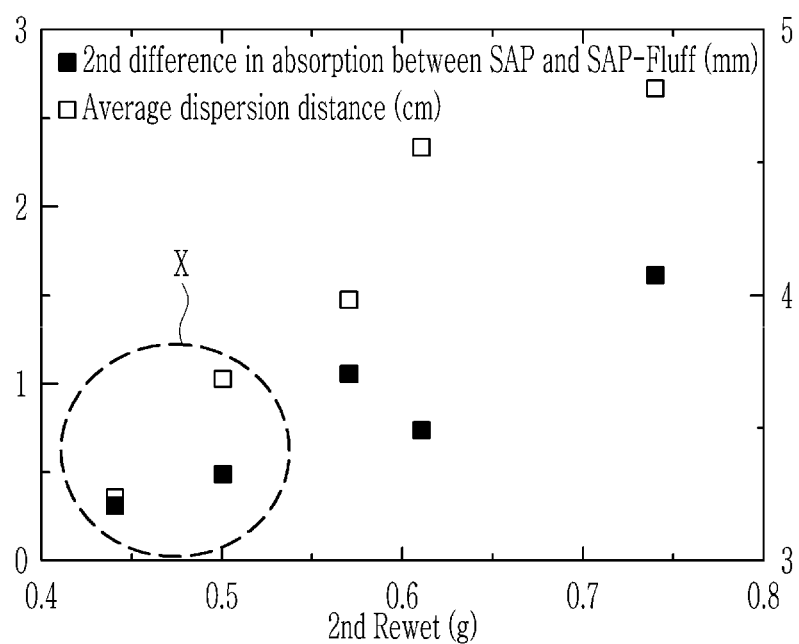

SAP EVALUATION APPARATUS

CROSS-REFERENCE TO RELATED APPLICATIONS

This application is a national phase entry under 35 U.S.C. § 371 of International Application No. PCT/KR2018/009823, filed Aug. 24, 2018, which claims priority to Korean Patent Application No. 10-2017-0108178, filed Aug. 25, 2017, and Korean Patent Application No. 10-2017-0121928, filed Sep. 21, 2017, the disclosures of which are hereby incorporated by reference.

TECHNICAL FIELD

The present invention relates to a SAP evaluation apparatus that effectively performs an evaluation of absorption and dispersion of SAPs or SAP composites, and evaluation of their quality.

BACKGROUND ART

Superabsorbent polymers were first commercialized for sanitary goods, and are now widely used for hygiene products such as disposable diapers for babies, horticultural soil water retention agents, materials for blocking water in engineering and construction work, sheets for use in the raising of seedlings, freshness-keeping agents in the food distribution industry, hot and cold therapy packs, and so on.

Superabsorbent polymers are widely used, especially for hygiene products such as diapers and sanitary pads.

Superabsorbent polymers must show more than a certain level of water absorbent capacity for use in hygiene products, and should not release absorbed liquid even under external pressure, for example, pressure from the weight of a diaper wearer.

Accordingly, there is a need to do a proper evaluation of the absorption or dispersion performance of superabsorbent polymers.

To evaluate the absorption or dispersion performance of superabsorbent polymers, a method using a difference in weight of a liquid before and after absorption or a method of measuring absorption characteristics by laser scanning has been used.

A dispersion evaluation was done in such a way that the length at which a liquid is dispersed over a SAP applied in a horizontal direction is measured.

However, the aforementioned evaluation method is problematic in that it has limitations in replicating the actual characteristics of diapers which absorb and disperse simultaneously.

Moreover, diapers are made from SAP composites, which are a blend of SAP and soft fluff. Thus, the characteristics of the fluff have a significant effect on the performance of diapers.

Accordingly, it is important to evaluate the physical properties of SAP composites containing fluff, as well as the physical properties of the SAP alone. However, conventional evaluation apparatuses only allow for evaluation of SAP but cannot evaluate SAP composites.

In addition, when diapers are worn, various pressures are applied depending on whether the wearer is standing, sitting, or lying down. This requires a technology that can adjust pressure depending on the wearer's position in evaluating the absorption/dispersion characteristics of diapers.

Further, since diapers are made from SAP composites, there is only a small correlation with the rate at which the diapers are rewetted with ink absorbed in superabsorbent polymers. Thus, conventionally, it is difficult to properly select a superabsorbent polymer with a low rewet rate or a SAP composite by evaluating superabsorbent polymers and SAP composites.

DISCLOSURE

Technical Problem

One aspect of the present invention is directed to providing a SAP evaluation apparatus that effectively performs an evaluation of the absorption, dispersion, and swelling characteristics of superabsorbent polymers (SAP) and SAP composites.

Another aspect of the present invention is directed to providing a SAP evaluation apparatus that allows for selecting a superabsorbent polymer or SAP composite of high quality.

Technical Solution

An exemplary embodiment of the present invention provides a SAP evaluation apparatus including: a main body installed with a lifting bar that is raised or lowered; a container portion installed under the lifting bar in the main body and having an internal containing space for containing an absorber; an operating portion connected to the lifting bar and having a lifting plate that is raised or lowered within the containing space and applies pressure to the absorber and an injection portion for injecting an ink in the direction of the absorber; a dispersion measurement portion for measuring dispersion of the ink through the absorber; and a controller attached to the main body to measure absorption of the ink into the absorber and measure swelling capacity of the absorber while the ink is injected into the absorber.

The container portion may be configured with an open top in such a way that the operating portion is raised from or lowered into the containing portion, and may be formed of a transparent material.

The operating portion includes: an injection body of which one side is connected to an end of the lifting bar, and that is formed with an injection portion; and a lifting plate connected to the other side of the injection body, with a bottom thereof making contact with the absorber.

The injection body may be formed with an ink injection hole on the side thereof, and the injection portion may protrude from under the injection body and lead to the injection hole to eject the ink therefrom.

The lifting plate may be connected to the side of the injection body with the injection portion penetrating therethrough, and the bottom makes contact with the absorber.

The controller may obtain a first measurement value by measuring the absorption height of the ink into the absorber while no pressure is applied to the absorber, and obtain a second measurement value by measuring the absorption height of the ink into the absorber while pressure is applied to the absorber.

The dispersion measurement portion may include a camera for capturing how the ink is dispersed into the absorber.

The controller may include a pressure sensor for measuring the swelling capacity of the absorber.

The absorber may be a superabsorbent polymer (SAP) or a SAP composite.

The controller may obtain a first height value at which the ink is absorbed into the superabsorbent polymer while the superabsorbent polymer is contained in the containing space, obtain a second height value at which the ink is absorbed into the SAP composite while the SAP composite is contained in the containing space, and determine that the SAP composite is in a normal condition if a difference between the first height value and the second height value is less than a first set distance and the dispersion distance of the ink through the SAP composite measured by the dispersion measurement portion is less than a second set distance.

The first set distance may be 0.7 mm.

The second set distance may be 3.9 cm when the SAP composite measures 100 mm wide and 20 mm long and 1.4 g of ink is injected.

Advantageous Effects

According to an exemplary embodiment of the present invention, it is possible to measure and evaluate in real time the absorption or dispersion of a solution, such as ink, into the superabsorbent polymer or SAP composite which is used in diapers or the like.

Furthermore, according to an exemplary embodiment of the present invention, it is possible to perform measurement and evaluation of absorption or dispersion while appropriate pressure is applied to the absorber, that is, the superabsorbent polymer (SAP) or SAP composite, thereby enabling effective evaluation.

In addition, according to an exemplary embodiment of the present invention, it is possible to effectively measure and evaluate the swollen gel strength of the absorber while pressure is applied to the absorber or no pressure is applied thereto, and therefore an effective evaluation of the performance of diapers made from the superabsorbent polymer (SAP) or SAP composite may be performed.

Further, according to an exemplary embodiment of the present invention, it is possible to effectively select a normal quality superabsorbent polymer or SAP polymer by easily checking whether the rate at which diapers are rewetted with ink absorbed in the superabsorbent polymer is within a set reference range. Accordingly, it is possible to easily determine whether the superabsorbent polymer and/or SAP polymer is in a normal condition or not, thereby enabling the development of diapers that provide a comfortable fit.

DESCRIPTION OF THE DRAWINGS

FIG. 1 is a schematic perspective view of essential parts of a SAP evaluation apparatus according to an exemplary embodiment of the present invention.

FIG. 2 is a schematic cross-sectional view of the essential parts when an operating portion is mounted on a container portion of FIG. 1.

FIG. 3 is a schematic cross-sectional view of the essential parts when an ink is injected into an absorber contained in the container of FIG. 2.

FIG. 4 is a schematic cross-sectional view of the essential parts when the ink is dispersed through the absorber contained in the container portion of FIG. 2.

FIG. 5 is a schematic cross-section view of the essential parts when the ink is dispersed further into the absorber of FIG. 4.

FIG. 6 is a schematic cross-sectional view of the essential parts when the absorber of FIG. 5 is swollen.

FIG. 7 is a graph showing changes over time in the absorption height of the ink while no pressure is applied to the lifting plate and while pressure is applied thereto.

FIG. 8 is a graph showing the absorption rate derived from the changes over time in the absorption height of the ink shown in FIG. 7.

FIG. 9 is a graph showing the dispersion area over time after injection of the ink.

FIG. 10 is a view of an image created by measuring the dispersion of the ink through the absorber.

FIG. 11 is a graph schematically showing the dispersion area derived through image analysis when the ink is dispersed through the SAP and SAP composite constituting the absorber.

FIG. 12 is a graph showing real-time measurements of the gel strength when the absorber is swollen while pressure is applied to the absorber and while no pressure is applied thereto.

FIG. 13 is a schematic cross-sectional view of the essential parts when the ink is injected and absorbed into the superabsorbent polymer contained in the container portion of FIG. 2.

FIG. 14 is a schematic cross-sectional view of the essential parts when the ink is injected into the SAP composite contained in the container portion of FIG. 2.

FIG. 15 is a graph schematically showing an average dispersion distance of ink through the SAP polymer and differences in absorption height between the superabsorbent polymer and SAP composite, in a plurality of products according to an exemplary embodiment of the present invention.

MODE FOR INVENTION

The present invention will be described more fully hereinafter with reference to the accompanying drawings, in which example embodiments of the invention are shown. As those skilled in the art would realize, the described embodiments may be modified in various different ways, all without departing from the spirit or scope of the present invention.

The drawings and description are to be regarded as illustrative in nature and not restrictive. Like reference numerals designate like elements throughout the specification.

Throughout this specification and the claims that follow, when it is described that an element is "connected" to another element, the element is "directly connected" to the other element or "indirectly connected" to the other element through a third element. In addition, unless explicitly described to the contrary, the word "comprise" and variations such as "comprises" or "comprising" will be understood to imply the inclusion of stated elements but not the exclusion of any other elements.

Throughout the specification, it will be understood that when an element such as a layer, film, region, or substrate is referred to as being "on" or "over" another element, it is directly on the other element or intervening elements may also be present. Further, in the specification, the word "on" or "over" means positioning on or below an object, and does not necessarily mean positioning on the upper side of the object based on the orientation with respect to the direction of gravity.

FIG. 1 is a schematic perspective view of essential parts of a SAP evaluation apparatus according to an exemplary embodiment of the present invention; FIG. 2 is a schematic cross-sectional view of the essential parts when an operating portion is mounted on the container portion of FIG. 2; FIG. 3 is a schematic cross-sectional view of the essential parts when an ink 44 is injected into an absorber contained in the container of FIG. 2; FIG. 4 is a schematic cross-sectional view of the essential parts when the ink 44 is dispersed through the absorber contained in the container portion of FIG. 2; FIG. 5 is a schematic cross-section view of the essential parts when the ink 44 is absorbed further into the absorber of FIG. 4; and FIG. 6 is a schematic cross-sectional view of the essential parts when the absorber of FIG. 5 is swollen.

As shown in FIGS. 1 to 6, a SAP evaluation apparatus 100 according to an exemplary embodiment of the present invention includes: a main body 10 installed with a lifting bar 20 that is raised or lowered; a container portion 30 installed under the lifting bar 20 in the main body 10 and including an internal containing space 31 for containing an absorber 50; an operating portion 40 connected to the lifting bar 20 and including a lifting plate 43 that is raised or lowered within the containing space 31 and applies pressure to the absorber 50 and an injection portion for injecting an ink 44 in the direction of the absorber 50; a dispersion measurement portion 70 for measuring the dispersion of the ink 44 through the absorber 50; and a controller 60 attached to the main body 10 to measure the absorption of the ink 44 through the absorber 50 and measure the swelling capacity of the absorber 50 while the ink 44 is injected into the absorber 50.

The absorber 50 to be described below refers to a superabsorbent polymer (hereinafter, SAP) 50a used in diapers or a SAP composite 50b made by blending the superabsorbent polymer 50 with fluff.

The absorption, dispersion, and swelling capacity of the absorber 50 may be measured while the absorber 50 is positioned in the container portion 30 as below. This will be described in detail below.

The main body 10 refers to a rheometer used to measure the viscosity or rheological properties of samples, which is installed on the bottom surface of a place of installation, and measures the absorption, dispersion, or swelling capacity of the absorber 50 while the absorber 50 is contained therein.

The main body 10 may have a measurement space 11 for measuring the absorption, dispersion, or swelling capacity of the absorber 50 while the absorber 50 is contained therein. The lifting bar 20 that is raised or lowered may be installed in the measurement space 11.

The lifting bar 20 may be installed in such a way that it is raised or lowered in the measurement space 11 by a driving portion (not shown) installed within the main body 10. The container portion 30 for containing the absorber 50 may be installed under the lifting bar 20.

The container portion 30, formed with the internal containing space 31 for containing the absorber 50, may be installed within the main body, with the top thereof being open. The operating portion 40, which is raised or lowered by the lifting bar 20, may be installed within the container portion 30 in such a manner so as to be raised or lowered while the absorber 50 is contained in the container portion 30.

The operating portion 40 may be connected to the lifting bar 20, and a lifting plate 43 that is raised or lowered within the containing space 31 and selectively applies pressure to the absorber 50 and an injection portion 42 for injecting an ink 44 in the direction of the absorber 50 may be formed in the lower part of the operating portion 40.

More specifically, the operating portion 40 may include an injection body 41 of which one side is connected to an end of the lifting bar 20, and that is formed with the injection portion 42, and a lifting plate 43 connected to the other side of the injection body 41, with the bottom making contact with the absorber 50.

The injection body 41, with one side being fixed to an end of the lifting bar 20, may have a cylindrical shape and be integrally or detachably fixed thereto. The injection body 41 is not necessarily limited to cylindrical shapes, and may have other appropriate shapes such as polygons.

Since the injection body 41 is fixed to an end of the lifting bar 20, it may be formed with the injection portion 42 for injecting the ink 44. Here, the ink 44 may be, but is not limited to, a solution made by dispersing pigments or dyes in saline (a solution of 0.90% w/v sodium chloride) to facilitate visual observation.

The injection portion 42 may protrude from under the injection body 41, and may internally have an ejection path for ejecting the ink 44. An injection hole 41a may be formed on the side of the injection body inlet 42 so as to eject the ink 44 through the injection portion 42. Accordingly, the ink 44 may be injected through the injection hole 41a and ejected from the injection portion 42 in the direction of the absorber 50.

Although one injection portion 42 protrudes from the injection body 41 by way of example, the present invention is not limited thereto, and at least two injection portions 42 may be formed and eject the ink 44 into the absorber 50.

The lifting plate 43 may be installed on the injection body 41.

The lifting plate 43 may be installed under the injection body 41, with a size corresponding to the plane area of the containing space 31 of the container portion 30. The reason why the lifting plate 43 is installed under the injection body 41 is to work in conjunction with the upward or downward movement of the lifting bar 20 and selectively apply pressure to the absorber 50. Here, the lifting plate 43 may form a pressure of up to 17 psi.

Further, the lifting plate 43 may be rotatably installed on the injection body 41 at a certain angular velocity.

The reason why pressure is applied to the absorber 50 using the lifting plate 32 is to embody a user sitting or lying down while wearing a diaper.

This way, the ink 44 may be injected into the container portion 30 through the operating portion 40, and the absorption of the ink 44 into the absorber 50 may be measured by the controller 60.

The controller 60 may obtain a first measurement value by measuring the absorption height of the ink 44 into the absorber 50 while no pressure is applied to the absorber 50, and obtain a second measurement value by measuring the absorption height of the ink 44 into the absorber 50 while pressure is applied to the absorber 50.

That is, the controller 60 may derive the first measurement value by injecting the ink 44 into the container portion 30 and measuring a change in the absorption height of the ink 44 while the lifting plate 43 has not moved down.

Then, the controller 60 may derive the second measurement value by injecting the ink 44 into the container portion 30, while the lifting plate 43 has moved down and pressure is applied to the absorber 50, and measuring a change in the absorption height of the ink 44.

Here, as the main body 10 functions as a rheometer, the controller 60 may measure changes in the absorption height of the ink 44. That is, the main body 10 may automatically measure the difference in the height of the lifting plate 43 before and after the absorber 50 is swollen by the absorption of the ink 44 into the absorber 50.

FIG. 7 is a graph showing changes over time in the absorption height of the ink 44 while no pressure is applied to the lifting plate and while pressure is applied thereto, and FIG. 8 is a graph showing the absorption rate derived from the changes over time in the absorption height of the ink 44 shown in FIG. 7.

As shown in FIG. 7 and FIG. 8, the absorption characteristics of the ink 44 while pressure is applied to the absorber 50 by using the lifting plate 43 and the absorption characteristics of the ink 44 while no pressure is applied to the absorber 50 may be measured and evaluated. Thus, it is possible to measure and evaluate the absorption characteristics in response to changes in the position of the user wearing a diaper, including when the user is sitting or lying down.

Meanwhile, the dispersion measurement portion 70 may measure the dispersion of the ink 44 through the absorber 50.

Here, the dispersion measurement portion 70 may include a camera for capturing how the ink 44 is dispersed into the absorber 50. The dispersion measurement portion and the camera will be denoted below by the same reference numeral.

As such, it is possible to capture an image of how the ink 44 is dispersed into the absorber 50 by using the camera 70 and derive the absorption rate through image analysis.

FIG. 9 is a graph showing the dispersion area over time after injection of the ink 44; FIG. 10 is a view of an image created by measuring the dispersion of the ink 44 through the absorber; and FIG. 11 is a graph schematically showing the dispersion area derived through image analysis when the ink 44 is dispersed through the SAP and SAP composite 50*b* constituting the absorber.

As shown in FIGS. 9 through 11, it is possible to easily measure and evaluate the dispersion area of the ink 44 while pressure is applied to the absorber 50 and while no pressure is applied thereto, by acquiring an image of how the ink 44 is dispersed through the absorber 50 by using the camera 70.

Meanwhile, the controller 60 may measure the swelling capacity of the absorber 50 while the ink 44 is injected into the absorber 50. That is, the controller 60 may measure swelling capacity by receiving a measurement signal from a pressure sensor 80 that measures the swelling capacity of the absorber 50.

Here, the pressure sensor 80 senses a pressure produced when the lifting plate 43 makes contact with the absorber 50. That is, it may sense a force exerted on the lifting plate 43. The pressure sensor 80 may be installed within the main body 10 of the rheometer or on the top of the lifting bar 20 to measure the swollen state of the absorber 50.

More specifically, the lifting plate 43 may apply constant pressure to the absorber 50, and its height may change as the volume of the absorber 50 expands. That is, as the absorber 50 swells up by absorbing the ink 44, it may push the lifting plate 43 in the opposite direction to where the lifting plate 43 applies pressure to the absorber 50.

Here, the controller 60 may check if the lifting plate 43 is raised by detecting the pressure by which the lifting plate 43 is pushed by the absorber 50. That is, if the force by which the lifting plate 43 is raised upward is greater than the force the lifting plate 43 exerts on the absorber 50, the controller 60 may determine that the height has increased and measure the height.

FIG. 12 is a graph showing real-time measurements of the gel strength when the absorber is swollen while pressure is applied to the absorber and while no pressure is applied to the absorber.

As shown in FIG. 12, it is possible to effectively measure and evaluate the swollen state of the absorber 50 while pressure is applied to the absorber 50 and while no pressure is applied thereto.

As described above, in the present exemplary embodiment, it is possible to measure and evaluate in real time the absorption or dispersion into the superabsorbent polymer 50*a* or SAP composite 50*b* which is used in diapers or the like.

Moreover, it is possible to perform a measurement and evaluation of absorption or dispersion while appropriate pressure is applied to the absorber 50, that is, the superabsorbent polymer (SAP) 50*a* or the SAP composite 50*b*, thereby enabling effective evaluation.

In addition, it is possible to effectively measure and evaluate the swollen gel strength of the absorber 50 while pressure is applied to the absorber 50 or no pressure is applied thereto, and therefore an effective evaluation of the performance of diapers made from the superabsorbent polymer (SAP) 50*a* or the SAP composite 50*b* may be performed.

Meanwhile, in an exemplary embodiment of the present invention, the controller 60 may measure the difference in the absorption height of the ink 44 into the superabsorbent polymer 50*a* or into the SAP composite 50*b* made from the superabsorbent polymer 50*a* or the dispersion distance of the ink 44, thereby enabling quality evaluation on the rewet characteristics.

The reason why the controller 60 measures the difference in the absorption height of the ink 44 into the superabsorbent polymer 50*a* or into the SAP composite 50*b* or the dispersion distance of the ink 44 is to check whether the superabsorbent polymer 50*a* used in diapers is in a normal, good quality condition or not.

Moreover, since a diaper is made from a SAP composite, the rate at which the diaper is rewetted with ink absorbed in the SAP composite 50*b* is affected by the characteristics of fluff contained in the SAP composite 50*b*. As such, the rewet characteristics of the SAP composite 50*b* may be effectively evaluated by detecting the characteristics of fluff contained in the SAP composite 50*b*.

First, as shown in FIG. 13, the controller 60 obtains a first height value (A) at which the ink 44 is absorbed into the superabsorbent polymer 50*a* while the superabsorbent polymer 50*a* constituting the absorber 50 is contained in the container portion 30.

Here, the main body 10 may function as a rheometer and measure the difference in the height of the lifting plate 43 before and after the superabsorbent polymer 50*a* is swollen, and the controller 60 may derive the first height value (A) by using the measurement made by the main body 10.

Afterwards, as shown in FIG. 14, the controller 60 obtains a second height value (a) at which the ink 44 is absorbed into the SAP composite 50*b* while the SAP composite 50*b* is contained in the container portion 30. Here, as described above, the second height value (a) may be obtained by using the rheometer function of the main body 10.

In this way, the controller 60 may measure the difference between the first height value (A) and the second height value (a), based on the measurements of the first height value (A) and the second height value (a) at which the ink 44 is absorbed into the superabsorbent polymer 50*a* and the SAP composite 50*b*, respectively.

Meanwhile, the controller 60 may determine whether the difference between the first height value (A) and the second height value (a) is less than a first set distance. If the difference between the first height value (A) and the second height value (a) is less than the first set distance, the controller 60 may measure the dispersion distance of the ink 44 absorbed into the SAP composite 50b. Of course, the controller 60 may appropriately change the order in which the dispersion distance and the difference between the first height value (A) and the second height value (a) are measured.

For example, if the difference between the first height value (A) and the second height value (a) is less than 0.7 mm, which corresponds to the first set distance, the controller 60 may determine that a first condition required for achieving the normal condition of the superabsorbent polymer 50a and/or the SAP composite 50b which may contain fluff is met. It should be noted that the first set distance may vary with circumstances.

Next, referring to FIG. 14, the controller 60 may receive a sensing signal of the dispersion distance (B) of the ink 44 absorbed through the SAP composite 50b from the dispersion measurement portion 70, and check whether the dispersion distance (B) is less than a second set distance.

Here, the controller 60 may receive a dispersion distance signal sensed by the dispersion measurement portion, i.e., the camera 70, and check whether the dispersion distance (B) is less than 3.9 cm, which corresponds to the second set distance. It should be noted that the second set distance may vary with circumstances.

By way of example, the measurement of the dispersion distance (B) of the ink 44 using the camera 70 is performed when the SAP composite 50b measures 100 mm wide and 20 mm long and 1.4 g of ink 44 is injected.

As described above, if the difference between the first height value (A) and second height value (a) at which the ink 44 is absorbed is less than 0.7 mm, which corresponds to the first set distance according to an exemplary embodiment of the present invention, and the dispersion distance (B) of the ink 44 through the SAP composite 50b is less than 3.9 mm, which corresponds to the second set distance according to an exemplary embodiment of the present invention, the controller 60 may determine that the superabsorbent polymer 50a and/or the SAP composite 50b which may contain fluff or the like is in a normal, good quality condition for the rewet characteristics.

That is, it is possible to effectively select a normal-quality superabsorbent polymer 50a and/or SAP polymer 50b that may contain fluff or the like, by checking whether the rate at which diapers are rewetted with ink absorbed in the superabsorbent polymer 50a is within a set reference range.

Accordingly, it is possible to easily determine whether the superabsorbent polymer 50a and/or the SAP polymer 50b that may contain fluff or the like is in normal condition or not, thereby enabling the development of diapers that provide a comfortable fit.

TABLE 1

|   | Difference in absorption height (mm) | Dispersion distance (cm) | Rewet rate (g) | If rewet criteria are met or not |
|---|---|---|---|---|
| A | 1.61 | 4.78 | 0.74 | X |
| B | 1.05 | 3.98 | 0.57 | X |
| C | 0.73 | 4.56 | 0.61 | X |
| D | 0.3 | 3.23 | 0.44 | ○ |
| E | 0.48 | 3.68 | 0.50 | ○ |

Meanwhile, the above table is a comparison table that shows the differences in absorption height between the superabsorbent polymer 50a and the SAP polymer 50b when the SAP polymer 50b measures 100 mm wide and 20 mm long and 1.4 g of ink is injected.

As shown in the above table of a comparison of the physical properties of A through E, it can be seen that D and E meet the conditions specifying that the difference in absorption height should be less than 0.7 mm, which corresponds to the first set distance according to an exemplary embodiment of the present invention, and the dispersion distance should be less than 3.9 cm, which corresponds to the second set distance according to an exemplary embodiment of the present invention.

Meanwhile, FIG. 15 is a graph schematically showing the differences in absorption height between the superabsorbent polymer 50a and the SAP polymer 50b, the average dispersion distance of ink through the SAP polymer 50b, and the rewet rate, in products A through E according to an exemplary embodiment of the present invention.

In the graph of FIG. 15, the vertical axis on the left represents the difference in absorption height measured in millimeters, the vertical axis on the right represents the dispersion distance measured in centimeters, and the horizontal axis represents the rewet rate measured in grams.

As shown in FIG. 15, it can be seen that a group of products, which correspond to D and E in Table 1, meet the conditions specifying that the difference in absorption height should be less than 0.7 mm and the dispersion distance should be less than 3.9 cm.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

10 . . . main body 11 . . . measurement space
20 . . . lifting bar 30 . . . container portion
31 . . . containing space 40 . . . operating portion
41 . . . injection body 41a . . . injection hole
42 . . . injection portion . . . lifting plate
50 . . . absorber 60 . . . controller
70 . . . dispersion measurement portion 80 . . . pressure sensor

The invention claimed is:

1. A superabsorbent polymer (SAP) evaluation apparatus comprising:
a main body installed with a lifting bar that is configured to be raised or lowered;
a container portion installed under the lifting bar in the main body, comprising an internal containing space configured to contain an absorber;
an operating portion connected to the lifting bar, comprising: a lifting plate that is configured to be raised or lowered within the internal containing space and to apply pressure to the absorber; and an injection portion configured to inject an ink in a direction of the absorber;
a dispersion measurement portion for measuring dispersion of the ink through the absorber; and
a controller installed on the main body configured to measure absorption of the ink into the absorber and to measure a swelling capacity of the absorber while the ink is injected into the absorber, wherein
the operating portion comprises:
an injection body of which a first side is connected to an end of the lifting bar, comprising the injection portion formed integrally therein; and
a lifting plate connected to a second side of the injection body, with a bottom thereof making contact with the absorber,
wherein the injection body comprises an ink injection hole on the second side thereof, and the injection portion protrudes from under the injection body and leads to the injection hole so as to be adapted to eject the ink therefrom.

2. The SAP evaluation apparatus of claim 1, wherein the container portion is configured with an open top and the operating portion is configured to be raised from or lowered into the containing space, and the container portion is formed of a transparent material.

3. The SAP evaluation apparatus of claim 1, wherein the controller is configured to obtain a first measurement value by measuring an absorption height of the ink into the absorber while no pressure is applied to the absorber, and is configured to obtain a second measurement value by measuring an absorption height of the ink into the absorber while pressure is applied to the absorber.

4. The SAP evaluation apparatus of claim 1, wherein the dispersion measurement portion comprises a camera configured to capture how the ink is dispersed into the absorber.

5. The SAP evaluation apparatus of claim 1, wherein the controller comprises a pressure sensor configured to measure the swelling capacity of the absorber.

6. The SAP evaluation apparatus of claim 1, wherein the absorber is one or more of a superabsorbent polymer (SAP) or a SAP composite.

7. A method of evaluating a SAP composite using the SAP evaluation apparatus of claim 6, comprising:
obtaining a first height value at which the ink is absorbed into the superabsorbent polymer while the superabsorbent polymer is contained in the containing space;
obtaining a second height value at which the ink is absorbed into the SAP composite while the SAP composite is contained in the containing space; and
determining that the SAP composite is in a normal condition if a difference between the first height value and the second height value is less than a first set distance and a dispersion distance of the ink through the SAP composite measured by the dispersion measurement portion is less than a second set distance.

8. The method of claim 7, wherein the first set distance is 0.7 mm.

9. The method of claim 7, wherein the second set distance is 3.9 cm. when the SAP composite measures 100 mm wide and 20 mm long and 1.4 g of ink is injected.

10. A superabsorbent polymer (SAP) evaluation apparatus comprising:
a main body installed with a lifting bar that is configured to be raised or lowered;
a container portion installed under the lifting bar in the main body, comprising an internal containing space configured to contain an absorber;
an operating portion connected to the lifting bar, comprising: a lifting plate that is configured to be raised or lowered within the internal containing space and to apply pressure to the absorber; and an injection portion configured to inject an ink in a direction of the absorber;
a dispersion measurement portion for measuring dispersion of the ink through the absorber; and
a controller installed on the main body configured to measure absorption of the ink into the absorber and to measure a swelling capacity of the absorber while the ink is injected into the absorber,
wherein the absorber is one or more of a superabsorbent polymer (SAP) or a SAP composite, and
wherein the controller is configured to: obtain a first height value at which the ink is absorbed into the superabsorbent polymer while the superabsorbent polymer is contained in the containing space; to obtain a second height value at which the ink is absorbed into the SAP composite while the SAP composite is contained in the containing space; and to determine that the SAP composite is in a normal condition if a difference between the first height value and the second height value is less than a first set distance and a dispersion distance of the ink through the SAP composite measured by the dispersion measurement portion is less than a second set distance.

11. The SAP evaluation apparatus of claim 10, wherein the first set distance is 0.7 mm.

12. The SAP evaluation apparatus of claim 11, wherein the second set distance is 3.9 cm when the SAP composite measures 100 mm wide and 20 mm long and 1.4 g of ink is injected.

* * * * *